United States Patent
Bonrath et al.

(10) Patent No.: US 6,423,851 B2
(45) Date of Patent: Jul. 23, 2002

(54) PREPARATION OF D,1-α-TOCOPHEROL

(75) Inventors: Werner Bonrath, Freiburg (DE); Shaoning Wang, Basel (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/932,519

(22) Filed: Aug. 17, 2001

Related U.S. Application Data

(63) Continuation of application No. 09/438,711, filed on Nov. 11, 1999, now abandoned.

(30) Foreign Application Priority Data

Nov. 11, 1998 (EP) .............................. 98121457

(51) Int. Cl.⁷ ........................................ C07D 311/72
(52) U.S. Cl. ..................................................... 549/411
(58) Field of Search ........................................ 549/411

(56) References Cited

U.S. PATENT DOCUMENTS

| | | | |
|---|---|---|---|
| 2,411,969 A | 12/1946 | Karrer et al. | |
| 3,444,213 A | 5/1969 | Nelan | |
| 3,459,773 A | 8/1969 | Moroe et al. | |
| 3,789,086 A | 1/1974 | Frick et al. | |
| 5,523,420 A | * 6/1996 | Lowack et al. | 549/411 |
| 5,908,939 A | * 6/1999 | Baak et al. | 549/407 |

FOREIGN PATENT DOCUMENTS

| | | |
|---|---|---|
| EP | 0 603 695 A1 | 12/1993 |
| EP | 0 658 552 A1 | 6/1995 |
| WO | WO 98/21197 | 5/1998 |

OTHER PUBLICATIONS

Ishihara et al., Synlett, Nov. 1996, (11), pp. 1045–1046.*
Patent Abstract of Japan, vol. 009, No. 309, abstract of JP 60149582 (1985).

* cited by examiner

*Primary Examiner*—Laura L. Stockton
(74) *Attorney, Agent, or Firm*—Bryan Cave LLP

(57) ABSTRACT

The present invention provides a process for preparing of d,l-α-tocopherol by the catalyzed condensation of trimethylhydroquinone with isophytol. This process includes carrying out the condensation in the presence of bis-(trifluoromethylsulphonyl)amine [$HN(SO_2CF_3)_2$] or a metal salt thereof of the formula Met $(N(SO_2CF_3)_2)_n$ (I) as the catalyst and supercritical carbon dioxide or nitrous oxide as the solvent, wherein Met is a metal atom such as for example boron, magnesium, aluminum, silicon, scandium, titanium, vanadium, manganese, iron, cobalt, nickel, copper, zinc, yttrium, zirconium, rhodium, palladium, silver, tin, lanthanum, cerium, neodymium, praseodymium, europium, dysprosium, ytterbium, hafnium, platinum and gold, and n is the corresponding valency (1, 2, 3, or 4) of the metal atom Met. A cosolvent may also be used, which is a lower aliphatic alkanol, ketone or hydrocarbon. The product of the process is the most active member of the vitamin E group.

11 Claims, No Drawings

PREPARATION OF D,1-α-TOCOPHEROL

This is a continuation of U.S. application Ser. No. 08/438,711 filed Nov. 11, 1999 now abandoned.

FIELD OF THE INVENTION

The present invention is concerned with a novel process for the manufacture of d,l-α-tocopherol by the catalyzed condensation of trimethylhydroquinone with isophytol in a solvent. As is known, d,l-α-tocopherol is a diastereomer mixture of 2,5,7,8-tetramethyl-2-(4',8',12'-trimethyltridecyl)-6-chromanol (α-tocopherol), which is the most active and industrially most important member of the vitamin E group.

BACKGROUND OF THE INVENTION

Many processes for the manufacture of d,l-α-tocopherol by the condensation of trimethylhydroquinone (TMHQ) with isophytol (IP) in the presence of various catalysts or catalyst systems and in various solvents are described in the literature. These processes go back to the work of Karrer et al., Bergel et al. as well as Smith et al. (see Helv. Chim. Acta 21, 520–525 (1938), Nature 142, 36 (1938) and, respectively, Science 88, 37–38 (1938) and J. Am. Chem. Soc. 61, 2615–2618 (1939)). While Karrer et al. carried out the synthesis of d,l-α-tocopherol from TMHQ and phytyl bromide in the presence of anhydrous zinc chloride ($ZnCl_2$; a Lewis acid), not only Bergel et al., but also Smith et al used TMHQ and phytol as starting materials.

In the following years modifications, such as alternative solvents and Lewis acids, were developed. From the work of Karrer et al. a process was developed in 1941 for the manufacture of d,l-α-tocopherol which was based on the condensation of TMHQ with IP in the presence of the catalyst system $ZnCl_2$/hydrochloric acid (HCl) (Karrer et al., U.S. Pat. No. 2,411,969). Later publications, e.g. Japanese Patent Publications (Kokai) 54380/1985, 64977/1985 and 226979/1987 (Chemical Abstracts (C.A.) 103, 123731s (1985), C.A. 103, 104799d (1985) and, respectively, C.A. 110, 39217r (1989)), disclose this condensation in the presence of zinc and $ZnCl_2$ and a Bronsted (protonic) acid, such as a hydrohalic acid, e.g. HCl, trichloroacetic acid, acetic acid and the like, especially $ZnCl_2$/HCl, as the catalyst system. Disadvantages of these and further published processes featuring $ZnCl_2$ in combination with a Bronsted acid are the corrosive properties of the acids and the contamination of the waste water with zinc ions as a result of the relatively large amount of $ZnCl_2$ required for the catalysis.

The manufacture of d,l-α-tocopherol by the reaction of TMHQ with phytyl chloride, phytol or isophytol in the presence of boron trifluoride ($BF_3$) or its etherate ($BF_3 \cdot Et_2O$) is disclosed in German Patents 960720 and 1015446 as well as in Nelan et al., U.S. Pat. No. 3,444,213, and Finnan, U.S. Pat. No. 4,634,781. However, $BF_3$ also has corrosive properties.

The condensation of TMHQ with IP or another phytyl derivative in the presence of a Lewis acid, e.g. $ZnCl_2$, $BF_3$ or aluminum trichloride ($AlCl_3$), a strong acid, e.g. HCl, and an amine salt as the catalyst system is disclosed in EP100471. In an earlier patent publication (DOS 2606830), the IP or phytol is pretreated with ammonia or an amine before the condensation with TMHQ in the presence of $ZnCl_2$ and an acid is effected. In both cases, corrosion problems occur.

A further interesting method for the manufacture of d,l-α-tocopherol from TMHQ and IP includes using an isolated TMHQ-$BF_3$ or -$AlCl_3$ complex as the catalyst and a solvent mixture featuring a nitro compound (see, DOS 1909164). This process avoids to a large extent the formation of undesired byproducts because it involves mild reaction conditions. The yield of d,l-α-tocopherol, based on IP and the use of the solvent mixture methylene chloride/nitromethane, is reported to be 77%. However, the use of such a solvent mixture is disadvantageous.

The manufacture of d,l-α-tocopherol by the condensation of TMHQ with IP using cation exchange resin complexes of metal ions ($Zn^{2+}$, $Sn^{2+}$ and $Sn^{4+}$) is disclosed in Bull. Chem. Soc. Japan 50, 2477–2478 (1977). One of the disclosed disadvantages is that the product is formed in unsatisfactory yields.

The use of macroreticular ion exchangers, e.g. AMBERLYST® 15, as the catalyst for the condensation of TMHQ with IP is disclosed in Moroe et al., U.S. Pat. No. 3,459,773. EP 603 695 discloses the manufacture of d,l-α-tocopherol in liquid or supercritical carbon dioxide by the condensation of TMHQ with IP in the presence of acidic catalysts, such as $ZnCl_2$/HCl and ion exchangers.

The condensation in the presence of a catalyst system which consists of iron(II) chloride, metallic iron and HCl gas is disclosed in DOS 2160103 and Frick et al., U.S. Pat. No. 3,789,086. The formation of fewer byproducts is an advantage of this process compared with the aforementioned process using $ZnCl_2$/HCl. However, corrosion problems and chloride contamination are equally disadvantageous.

An alternative for the condensation of TMHQ with IP to d,l-α-tocopherol including using trifluoroacetic acid or its anhydride as the catalyst is disclosed in EP 12824. Although this process avoids the use of HCl, the alternative catalyst is relatively expensive.

The use of heteropolytungsten acids as catalysts for the condensation of TMHQ with IP is disclosed in React. Kinet. Catal. Lett. 47(1), 59–64 (1992). d,l-α-Tocopherol was reportedly obtained with about 90% yield using this process and various solvents. A further process disclosed in the literature (EP 658 552; Bull. Chem. Soc. Japan 68, 3569–3571 (1995)) for the synthesis of d,l-α-tocopherol is based on the use of a scandium, yttrium or lanthanide fluorosulphonate, nitrate or sulphate, e.g. scandium trifluoromethanesulphonate. With up to about 10% excess of IP this process reportedly achieves yields up to 98%.

The use of ion exchanged bentonite, montmorillonite or saponite through treatment with, e.g. scandium chloride and other metal salts (yttrium, lanthanum, etc.) as the catalyst for the condensation of TMHQ with IP has as a disadvantage the need for a large amount of catalyst (EP 677 520; Bull. Chem. Soc. Japan 69, 137–139 (1996)). According to the Examples of EP 694 541, the condensation of TMHQ with IP to form α-tocopherol may be achieved in high yields and with a high product purity when solvents such as carbonate esters, fatty acid esters and mixed solvent systems are employed, wherein catalysis is effected by $ZnCl_2$/HCl. Disadvantages in this process include, in addition to the contamination of the waste water by zinc ions, the usual large "catalyst amount" of $ZnCl_2$ used.

According to WO 97/28151, the acid catalyzed condensation of TMHQ with IP may be performed in a cyclic carbonate or α-lactone as the solvent. The preferred catalyst is a mixture of ortho boric acid and oxalic, tartaric or citric acid, or boron trifluoride etherate.

Finally, WO 98/21197 discloses the manufacture of d,l-α-tocopherol from TMHQ and IP using bis (trifluoromethylsulphonyl)amine or a metal salt thereof optionally with a strong Bronsted acid as catalyst in a variety of aprotic solvents such as aliphatic and cyclic ketones or esters, and aromatic hydrocarbons.

From the foregoing explanations it is evident that most of the previously known processes have considerable disadvantages. Thus, corrosion problems occur in the case of all processes in which acid catalysts such as boron trifluoride are used. Toxicity problems with the boron trifluoride adducts also occur. When iron or zinc is used, there is a contamination of the waste water with the metal ions which today is no longer acceptable. In some of the prior art processes, formation of undesired byproducts, e.g. phytyl-toluene and chlorophytols, is an especially serious problem. Furthermore, the use of organic solvents requires complicated procedures for their removal or recycling during the product isolation.

SUMMARY OF THE INVENTION

An object of the present invention is to provide a process for the preparation of d,l-α-tocopherol by the condensation of trimethylhydroquinone with isophytol in the presence of a catalyst and in a solvent which does not have the disadvantages of previously known procedures. In this respect, it is necessary that the catalyst used does not have a corrosive action, is non-toxic, does not contaminate the environment, catalyzes as selectively as possible the desired reaction in small, catalytic amounts and in high yields, and should be readily separable and re-usable several times. The solvent should allow more ready isolation of the product than has previously been achieved in using organic solvents.

Accordingly, the present invention provides a process for synthesizing d,l-α-tocopherol by catalyzed condensation reaction of trimethylhydroquinone with isophytol, comprising reacting trimethylhydroquinone with isophytol in a reaction mixture containing a catalyst comprising bis-(trifluoromethylsulphonyl)amine of the formula

or a metal salt thereof having the formula

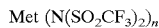           I wherein

Met is a metal atom selected from the group consisting of boron, magnesium, aluminum, silicon, scandium, titanium, vanadium, manganese, iron, cobalt, nickel, copper, zinc, yttrium, zirconium, rhodium, palladium, silver, tin, lanthanum, cerium, neodymium, praseodymium, europium, dysprosium, ytterbium, hafnium, platinum and gold; and n is the corresponding valency (1, 2, 3 or 4) of the metal atom Met, and supercritical carbon dioxide or nitrous oxide as the solvent.

DETAILED DESCRIPTION OF THE INVENTION

The present invention is achieved by carrying out the condensation of trimethylhydroquinone with isophytol in the presence of a particular amine catalyst and in supercritical carbon dioxide or nitrous oxide. The condensation itself is represented in the following Reaction Scheme:

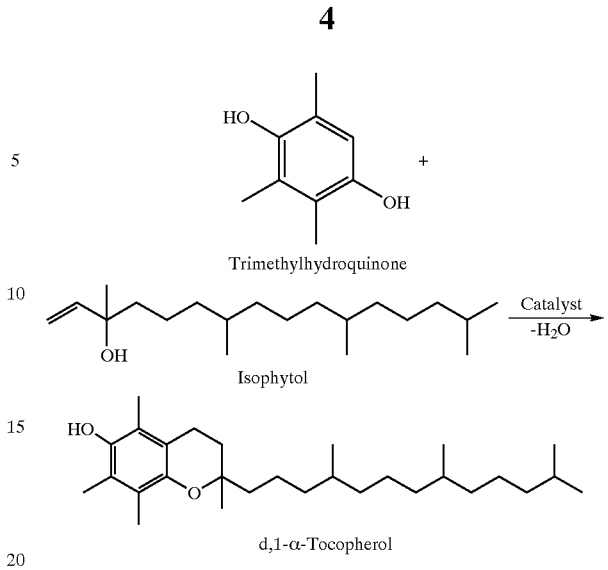

The process of the present invention for synthesizing d,l-α-tocopherol by the catalyzed condensation of trimethylhydroquinone with isophytol includes carrying out the condensation in the presence of bis-(trifluoromethylsulphonyl)amine of the formula

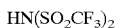

or a metal salt thereof having the formula I

           I wherein

Met is a metal atom selected from boron, magnesium, aluminum, silicon, scandium, titanium, vanadium, manganese, iron, cobalt, nickel, copper, zinc, yttrium, zirconium, rhodium, palladium, silver, tin, lanthanum, cerium, neodymium, praseodymium, europium, dysprosium, ytterbium, hafnium, platinum and gold and n is the corresponding valency (1, 2, 3 or 4) of the metal atom Met, as the catalyst and in supercritical carbon dioxide or nitrous oxide as the solvent.

Bis-(trifluoromethylsulphonyl)amines, and a number of the metal salts of formula I are known (see, for example, EP 364 340, Japanese Patent Publication (Kokai) 246 338/1995, DOS 19533711, Synlett 1996, 171–172, Synlett 1996, 265–266, Chem. Lett. 1995, 307–308 as well as the literature cited therein).

The new metal salts of formula I may be produced according to methods known in the art, such as, for example, from the corresponding metal acetates, oxides, hydroxides and alcoholates which are similar to the methods for producing the known compounds. In the case of the aluminum salt and the zinc salt of bis-(trifluoromethylsulphonyl)amine (of the formula Al[N(SO$_2$CF$_3$)$_2$]$_3$ and Zn[N(SO$_2$CF$_3$)$_2$]$_2$, respectively), these salts can also be produced from a corresponding alkylmetal or dialkylmetal hydride, e.g. diethylzinc or triethylaluminum, or diisobutylaluminum hydride, respectively.

The metal salts of the bis-(trifluoromethylsulphonyl) amine may be present in the condensation reaction in monomeric or polymeric form. Accordingly, formula I is intended to embrace all such forms. Further, these catalysts may be used in isolated form or produced in situ.

As used herein, the expression "supercritical carbon dioxide" is to be understood as indicating carbon dioxide which is present at a temperature and pressure exceeding its critical temperature of 31° C. and its critical pressure of 73.8 bar (7.38 MPa). Analogously, "supercritical nitrous oxide" is understood to indicate nitrous oxide which is present at a temperature and pressure exceeding its critical temperature of 36.5° C. and its critical pressure of 72.6 bar (7.26 MPa). Both substances are ecologically acceptable and are excellent solvents in the supercritical state for both the reactants and the product of the process according to the present invention.

A cosolvent may also be used in the process of the present invention, said cosolvent being an organic protic or aprotic solvent. Those organic solvents, which are especially useful as the cosolvent, include for example, lower aliphatic alkanols, e.g. methanol and ethanol; lower aliphatic ketones, e.g. acetone, isobutyl methyl ketone and diethyl ketone; and lower aliphatic hydrocarbons, e.g. propane.

If a cosolvent is employed, the ratio (by weight) of the cosolvent to supercritical carbon dioxide or nitrous oxide is in the range from about 1:30 to about 1:1, preferably in the range from about 1.2:30 to about 9:30.

With due consideration to the necessity for carrying out the condensation of trimethylhydroquinone with isophytol according to the process of the present invention at temperatures and pressures which enable the solvent to be maintained in the supercritical state, the condensation may be carried out at temperatures/pressures of about 40° C. to about 200° C./about 80 to about 270 bar (about 8 to about 27 MPa), preferably at temperatures/pressures of about 110° C. to about 160° C./about 130 to about 170 bar (about 13 to about 17 MPa). These parameters apply regardless of whether supercritical carbon dioxide or supercritical nitrous oxide is used as the solvent. These same conditions apply where a cosolvent is also employed.

In the present invention, the molar ratio of trimethylhydroquinone to isophytol present in the reaction mixture for condensation extends from about 0.8:1 to about 1.2:1; this molar ratio of trimethylhydroquinone:isophytol is preferably from about 0.9:1 to about 1.1:1, most preferably about 1:1 (as near to equimolar amounts as possible).

The amount of catalyst used in the present invention is calculated so that the molar ratio of the catalyst to the educt which is in the lesser molar amount (trimethylhydroquinone or isophytol, whichever is in the lesser molar amount) is about 1:1000 to about 1:100. In the case of the bis-(trifluoromethylsulphonyl)amine, the ratio is preferably about 1:500. In the case of a metal salt of formula I, the ratio is preferably about 1:200.

Regarding the amount of supercritical carbon dioxide or nitrous oxide used, in both cases the weight ratio of supercritical carbon dioxide or nitrous oxide to the educt (trimethylhydroquinone or isophytol) which is in the lesser molar amount is about 2:1 to about 8:1, preferably about 5:1 to about 8:1, for example, about 6:1. Where a cosolvent is also employed, the total weight of supercritical carbon dioxide or nitrous oxide and cosolvent is increased in accordance with the previously indicated weight ratio of cosolvent to the supercritical solvent.

The actual condensation reaction generally lasts for about 1–5 hours, preferably about 2–4 hours, such as for example about 2.5–3 hours.

The process in accordance with the invention may be carried out operationally by heating together the two educts (trimethylhydroquinone and isophytol), the catalyst and a sufficient amount of carbon dioxide or nitrous oxide, optionally with cosolvent, in, for example, an autoclave to maintain the temperature and pressure at a level at which the supercritical state is constantly present. After completion of the condensation reaction, the autoclave is then cooled to room temperature and the pressure released. The crude product may be dissolved in a suitable organic solvent, such as a lower alkanol, e.g. methanol, and the solution concentrated under reduced pressure to isolate the product. At this stage, the product may be analyzed for purity, if desired, by a standard analytical method, e.g. gas chromatography.

The process in accordance with the invention enables the catalyst used to be separated readily and to be re-used several times.

Advantages in the use of the combination of the catalyst and supercritical solvent in the process in accordance with the invention are, in addition to high yields of d,l-α-tocopherol, the avoidance of corrosion, the avoidance of waste water contamination with heavy metal ions, the high selectivity, as well as the ready isolation of the d,l-α-tocopherol product from the mixture after the reaction.

The following examples are provided to further illustrate the process of the present invention in some of its embodiments. These examples are illustrative only and are not intended to limit the scope of the invention in any way.

EXAMPLES

Examples 1–10

General Procedure for Batch Process

In a stainless steel autoclave (35 ml: "smaller" scale; or 170 ml: "larger" scale) equipped with a magnetic or mechanical stirrer, a mixture of trimethylhydroquinone (1.52 g, 9.79 mmol based on 98% pure educt: "smaller" scale; or 7.38 g, 47.52 mmol based on 98% pure educt: "larger" scale), isophytol (approx. 3 g/3.8 ml, approx. 9.6 mmol based on 96% pure educt: "smaller" scale; or 14.92 g/18.4 ml, 46.46 mmol based on 96% pure educt: "larger" scale), a varied amount of catalyst, and a varied amount of solvent (supercritical $CO_2$ or $N_2O$) was heated with stirring from room temperature to 150° C. and the pressure at the higher temperature measured. The reaction mixture was maintained at 150° C. for 3 hours, and thereafter cooled to room temperature. After releasing the pressure in the autoclave, the contents of the autoclave were worked up by dissolution in methanol and evaporation under reduced pressure. The product was then analyzed by a standard gas chromatographic method to determine the yield of d,l-α-tocopherol achieved.

The further details of the experimentally performed process and the corresponding yields of d,l-α-tocopherol achieved are presented in Table I:

TABLE I

| Example | Scale | Catalyst, amount in mg | Solvent, weight in g | Pressure in bar | Percentage yield |
|---|---|---|---|---|---|
| 1 | Smaller | $HN(SO_2CF_3)_2$, 10.0 | $CO_2$, 3.7 | 75 | 84.6 |
| 2 | Smaller | $HN(SO_2CF_3)_2$, 1.5 | $CO_2$, 3.8 | 75 | 79.8 |
| 3 | Smaller | $HN(SO_2CF_3)_2$, 10.0 | $CO_2$, 9.5 | 160 | 86.4 |
| 4 | Smaller | $HN(SO_2CF_3)_2$, 10.0 | $CO_2$, 15.2 | 225 | 85.4 |
| 5 | Smaller | $HN(SO_2CF_3)_2$, 10.0 | $N_2O$, 10.0 | 155 | 88.3 |
| 6 | Larger | $HN(SO_2CF_3)_2$, 48.6 | $N_2O$, 48.6 | 160 | 89.6 |
| 7 | Smaller | $AgN(SO_2CF_3)_2$, 10.0 | $CO_2$, 3.8 | 85 | 81.4 |
| 8 | Smaller | $AgN(SO_2CF_3)_2$, 65.0 | $CO_2$, 11.6 | 160 | 81.8 |
| 9 | Smaller | $AgN(SO_2CF_3)_2$, 10.0 | $N_2O$, 10.0 | 160 | 89.0 |
| 10 | Larger | $AgN(SO_2CF_3)_2$, 32.4 | $N_2O$, 48.6 | 160 | 83.1 |

(1 bar = 0.1 MPa)

Example 11

This Example illustrates a semi-batch procedure for the process of the present invention.

A mixture of 15.2 g (98%, 100 mmol) of trimethylhydroquinone, 100.2 mg of $NH(SO_2CF_3)_2$, 10 ml (8.11 g, 96%, 25.22 mmol) of isophytol, and 48.6 g $CO_2$ in a 380 ml autoclave equipped with a mechanical stirrer was heated from room temperature to 150° C., after which the pressure was 85 bar (8.5 MPa). Additional isophytol (27 ml, 21.9 g, 68.2 mmol) was added within 85 minutes and the reaction mixture was stirred for 90 minutes more. After completion of the reaction, the autoclave was cooled to room temperature. The reaction mixture was then collected and concentrated in vacuo. The crude product was analyzed by gas chromatography, which indicated that a 84.23% yield of d,l-α-tocopherol had been obtained.

The invention being thus described, it will be obvious that the same may be varied in many ways. Such variations are not to be regarded as a departure from the spirit and scope of the invention, and all such modifications are intended to be included within the scope of the following claims.

We claim:

1. A process for synthesizing d,l-α-tocopherol by catalyzed condensation reaction of trimethylhydroquinone with isophytol, comprising reacting trimethylhydroquinone with isophytol in a reaction mixture containing a catalyst comprising bis(trifluoromethylsulphonyl)amine of the formula

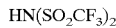

$HN(SO_2CF_3)_2$ or a metal salt thereof having the formula

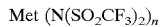

Met $(N(SO_2CF_3)_2)_n$   I wherein

Met is a metal atom selected from the group consisting of boron, magnesium, aluminum, silicon, scandium, titanium, vanadium, manganese, iron, cobalt, nickel, copper, zinc, yttrium, zirconium, rhodium, palladium, silver, tin, lanthanum, cerium, neodymium, praseodymium, europium, dysprosium, ytterbium, hafnium, platinum and gold; and n is the corresponding valency (1, 2, 3 or 4) of the metal atom Met, as the catalyst and supercritical carbon dioxide or nitrous oxide as the solvent;

2. A process according to claim 1 wherein the reaction mixture further contains a cosolvent which is a lower aliphatic alkanol, a lower aliphatic ketone or a lower aliphatic hydrocarbon.

3. A process according to claim 2 wherein the cosolvent is selected from the group consisting of methanol, ethanol, acetone, isobutyl methyl ketone, diethyl ketone and propane.

4. A process according to claim 1 wherein the condensation reaction is carried out at a temperature of about 40° C. to about 200° C. and a pressure of about 80 to about 270 bar.

5. A process according to claim 4 wherein the condensation reaction is carried out at a temperature of about 110° C. to about 160° C. and a pressure of about 130 bar to about 170 bar.

6. A process according to claim 1 wherein a molar ratio of trimethylhydroquinone to isophytol in the reaction mixture is from about 0.8:1 to about 1.2:1.

7. A process according to claim 6 wherein the molar ratio of trimethylhydroquinone to isophytol in the reaction mixture is from about 0.9:1 to about 1.1:1.

8. A process according to claim 7 wherein the molar ratio of trimethylhydroquinone to isophytol in the reaction mixture is about 1:1.

9. A process according to claim 1 wherein the molar ratio of catalyst to trimethylhydroquinone or isophytol, whichever is present in the reaction mixture in a lesser amount, is about 1:1000 to about 1:100.

10. A process according to claim 1 wherein the weight ratio of the supercritical carbon dioxide or nitrous oxide to trimethylhydroquinone or isophytol, whichever is present in the reaction in a lesser amount, is from about 2:1 to about 8:1.

11. A process according to claim 10 wherein the weight ratio of the supercritical carbon dioxide or nitrous oxide to trimethylhydroquinone or isophytol, whichever is present in the reaction in a lesser amount, is from about 5:1 to about 8:1.

* * * * *

UNITED STATES PATENT AND TRADEMARK OFFICE
CERTIFICATE OF CORRECTION

PATENT NO. : 6,423,851 B2  
DATED : July 23, 2002  
INVENTOR(S) : Werner Bonrath et al.

It is certified that error appears in the above-identified patent and that said Letters Patent is hereby corrected as shown below:

<u>Title page,</u>  
Item [54], please change "1" to -- L --.

Signed and Sealed this

Tenth Day of December, 2002

JAMES E. ROGAN  
*Director of the United States Patent and Trademark Office*